United States Patent [19]

Yano et al.

[11] Patent Number: 4,474,183

[45] Date of Patent: Oct. 2, 1984

[54] GAS SENSOR

[75] Inventors: Makotao Yano, Kurashiki; Michihiro Nakamura, Soja, both of Japan

[73] Assignee: Kuraray Co., Ltd., Kurashiki, Japan

[21] Appl. No.: 567,559

[22] Filed: Jan. 3, 1984

[30] Foreign Application Priority Data

Jan. 17, 1983 [JP] Japan .................................. 58-6120

[51] Int. Cl.³ ...................... G01N 27/30; G01N 27/40
[52] U.S. Cl. .................................... 128/635; 204/403; 204/415
[58] Field of Search ................ 128/635; 204/403, 415, 204/1 K, 1 S; 357/25

[56] References Cited

U.S. PATENT DOCUMENTS 3,719,576  3/1973  Macur .............................. 204/415 X
4,273,636  6/1981  Shimada et al. ..................... 204/415
4,409,980 10/1983  Yano et al. ........................ 128/635

Primary Examiner—G. L. Kaplan
Attorney, Agent, or Firm—Oblon, Fisher, Spivak, McClelland & Maier

[57] ABSTRACT

A gas sensor with its photosensitivity allayed in which a hydrogen ion sensitive FET transducer having the structure of a gate-insulated field effect transistor and an Ag-AgCl reference electrode are housed inside a flexible tube in such a way that the gate part of said FET transducer and the reference electrode are located at the front end opening of the tube or an opening provided in the side wall of the tube; while the lead wires connected to the FET transducer and the reference electrode are extended along the tube, this tube is closed by filling an electrical insulation resin at least in the space of the part inside the tube wall housing the parts connecting the lead wires to the aforementioned FET transducer and to the reference electrode; further, a hydrophilic polymer containing an electrolyte is put around at least the gate part of said FET and part of the reference electrode, to envelop both of them; and whole of the surface of the aforementioned hydrophilic polymer and that of at least the part of the insulator tube housing the FET transducer are coated with a gas permeable membrane formed of a colored silicone rubber with a low optical transmittance.

5 Claims, 8 Drawing Figures

GAS SENSOR

BACKGROUND OF THE INVENTION

1. Field of the Invention

The present invention relates to a gas sensor of Severinghaus type using a hydrogen ion sensitive FET transducer of the structure of an oblong gate-insulated field effect transistor having its gate part at the front end and its electrode part at the other end.

2. Description of the Prior Art

The measurement of concentration of gas such as carbon dioxide or ammonia gas is, of course, important in industrial applications, but recently in the medical field, the measurement of partial pressure of gas in living bodies begins to be taken seriously. For example, in medicine, continuous measurements of gas partial pressure in blood of anesthetized patients, those with advanced diseases or those in the convalescent stage are lending themselves to discovery of emergent situations. For such purposes, a very small gas sensor with less than 2 mm diameter which may be inserted in any blood vessel or muscle tissue is required.

For the aforementioned purpose, heretofore in use has been a gas sensor of the Severinghaus type using a very small glass electrode. Minuaturization of the glass electrode, however, is known to involve following problems:

(a) Because the resistance of the glass film is approx. 10 MΩ, an amplifier with a high input impedance is necessary.

(b) The glass film, being thin, has low mechanical strength.

(c) Because of the electrode area being small, the resistance of the glass film is large.

The measuring instruments should be large and complex and the electrodes themselves are brittle and tend to break. Therefore, especially as a sensor to be inserted into tissues of living bodies for measuring gas partial pressure in living bodies, this instrument has posed a problem in practical applications.

On the other hand, a carbon dioxide gas sensor using a solid pH electrode of metal oxide in place of the glass electrode is disclosed in U.S. Pat. No. 3,719,576, etc. This sensor is smaller and slenderer than that using a glass electrode and is, therefore, suitable as a sensor to be inserted in living tissues, but has the following disadvantages:

(a) Because of the use of the solid electrode, sensor is inflexible.

(b) Its electric resistance is increased due to the miniaturization.

On this ground, the miniaturization had its limit.

This problem has been solved by making use of a hydrogen ion sensitive FET transducer (hereinafter referred to as pH-ISFET) having the gate-insulated field effect transistor structure described in U.S. Pat. No. 4,218,298 in place of the glass electrode of the solid electrode. Such a gas sensor using the pH-ISFET is, as described in U.S. Pat. No. 4,409,980, a gas sensor composed of a pH-ISFET and a reference electrode deposited on the substrate in proximity to the gate part of the pH-ISFET, an insulator tube housing this pH-ISFET and the reference electrode with lead wires connected thereto, the gate part of the aforementioned pH-ISFET being located at an opening part provided in the insulator tube, and the lead wires extended along the tube, an electrical insulation resin closing the tube by filling the space of the part inside the tube wall housing the lead wire connecting parts, a hydrophilic polymer layer containing electrolytes which undergo change in hydrogen ion concentration, as it absorbs the gas, and which is placed around the gate part of the pH-ISFET and the reference electrode, enveloping both of them, and a gas permeable membrane coating at least whole of the aforementioned polymer layer.

The aforementioned gas sensor is preferable as a gas sensor to be inserted in living bodies. However, the pH-ISFET usually has a photo-sensitivity of the order of $10^{-5}-10^{-6}$ V/lux. Therefore, when a gas sensor using the pH-ISFET is used for monitoring, etc., during operation, when it receives illumination of several thousands luxes - several tens of thousands luxes, the photosensitivity of the pH-ISFET poses a serious obstacle to its practical use.

Coating the gate part of the pH-ISFET with a hydrophilic polymer colored black for allaying the photosensitivity of the pH-ISFET is described in U.S. Pat. No. 4,273,636. However, the aforementioned proposal is to allay the photosensitivity of ion sensor using ISFET and does not relate to a gas sensor. It is in principle practicable to allay the photosensitivity of a gas sensor by utilizing a pH-ISFET with a hydrophilic polymer colored black coated on its gate part. In this instance, the gate part of the pH-ISFET and the reference electrode are enclosed by a hydrophilic polymer containing a gas absorbing liquid colored black and the outside of this polymer is coated with a gas permeable membrane. It has become evident, however, that diminishing the photosensitivity of a gas sensor by this method involves the following problems:

(1) The photosensitivity of pH-ISFET exists not only on its gate part but on whole of the Si substrate including its electrode part. Accordingly, it is difficult to totally eliminate the photosensitivity by coating only the gate part with a black polymer, as above described.

(2) In the Severinghaus gas sensor, the partial pressure of gas is measured by utilizing the minute change of pH of the gas absorbing liquid. Accordingly, it is necessary to avoid changes of pH of the gas absorbing liquid due to factors other than the gas partial pressure. However most of such black pigments, being chemically unstable, will become acidic due to autoxidation, etc., during a long period of storage, often inviting changes in characteristics as a gas sensor. Accordingly, using the pH-ISFET with its gate part coated with a hydrophilic polymer colored black for allaying the photosensitivity of the pH-ISFET is problematical in practical applications as a gas sensor.

The present inventors have found out the improved gas sensor of this invention as a result of investigations carried out for providing a practically useful gas sensor in which the photosensitivity of the gas sensor of the Severinghaus type using pH-ISFET is allayed.

SUMMARY OF THE INVENTION

An object of this invention is to provide a gas sensor which always gives stable and correct measured values for a long period without being sensitive to light.

Another object of this invention is to provide a miniature gas sensor which is insertable in living bodies.

A further object of this invention is to provide a gas sensor which is easy to manufacture and adaptable for mass production.

The gas sensor of this invention is composed of a hydrogen ion sensitive FET transducer of an oblong gateinsulated field effect transistor structure having its gate part at the front end and its electrode parts at the other end, an Ag-AgCl reference electrode located adjacent to the gate part of the aforementioned transducer, an insulator tube housing the FET transducer and the reference electrode with one end of each lead wire connected thereto, the FET transducer and the reference electrode being located at the opening part of the insulator tube, and the lead wires extended along the tube, with a connector attached to the other ends of said lead wires, an electrically insulative resin filled at least in the space of the part inside the tube wall housing the lead wire connecting parts, thereby closing the tube, a hydrophilic polymer layer containing electrolytes which undergo change in its hydrogen ion concentration, as it absorbs the gas, said layer being put around the gate part of the FET transducer and the reference electrode, enveloping both of them, and a gas permeable membrane formed of a colored silicone rubber which gives an optical transmittance less than 10% to a light of 400–1,200 nm and the division (P/d) of the nitrogen gas permeability (P) by the film thickness (d) more than $2.5 \times 10^{-7}$ [$cm^3(STP)/cm^2 \cdot sec \cdot cmHg$], said membrane coating whole of the aforementioned hydrophilic polymer layer and whole of the surface of at least the part of the insulator tube in which the FET transducer is housed.

DETAILED DESCRIPTION OF THE PREFERRED EMBODIMENTS

Figure 1:
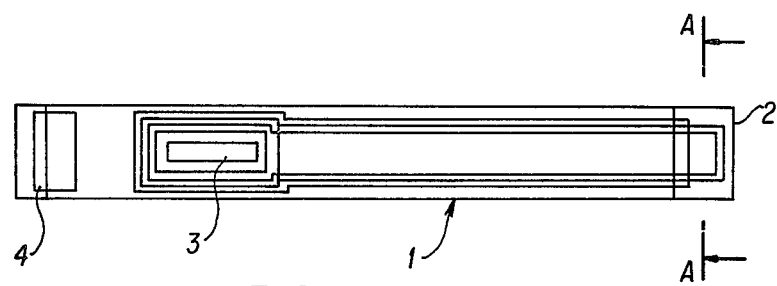
FIG. 1 is a plane view of a pH-ISFET used in the gas sensor of this invention.
Figure 2:
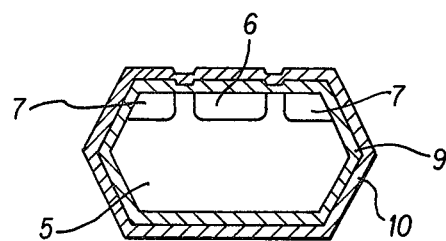
FIG. 2 is a sectional view along A—A of the pH-ISFET shown in FIG. 1.

FIG. 1 is a plane view illustrating a pH-ISFET 1 used in the gas sensor of this invention. This pH-ISFET 1 is, for example, of an oblong shape of 0.4 mm width and 3–4 mm length and is provided with its gate part 2 at one end and with drain terminal 3 and source terminal 4 at the other end. With regard to a particular structure of pH-ISFET, reference is made to that of U.S. Pat. No. 4,218,298. The gate part 2, as shown in FIG. 2, a sectional view along A—A of FIG. 1, is composed by forming in a silicon substrate 5 a drain diffusion region 6 and source diffusion region 7 and coating the whole successively with an oxide film 9 and a surface stabilizing film 10. As this surface stabilizing film 10, one of films of silicon nitride ($Si_3N_4$), alumina ($Al_2O_3$), tantalum pentoxide ($Ta_2O_5$), etc., may be utilized and sensors having the aforementioned films are sensitive to hydrogen ion. Actually, by using a silicon nitride film of the order of 1,000 Å as the surface stabilizing film, a surface potential of 53–56 mV/pH which is nearly the same level as that of the conventional glass electrode is obtained in a range of pH 1 - pH 13.

Figure 3A:
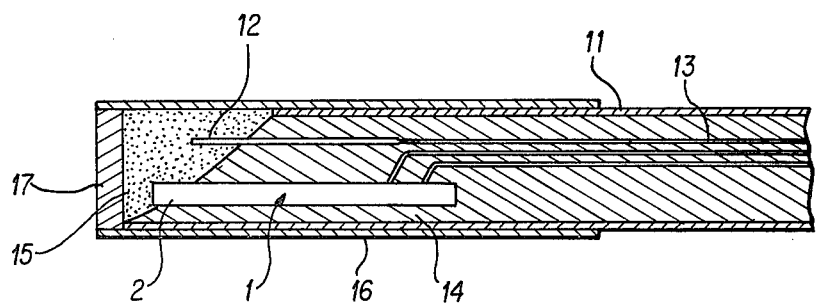
FIGS. 3a, 3b and 4 are sectional views of the principal parts of gas sensors of this invention.
Figure 3B:
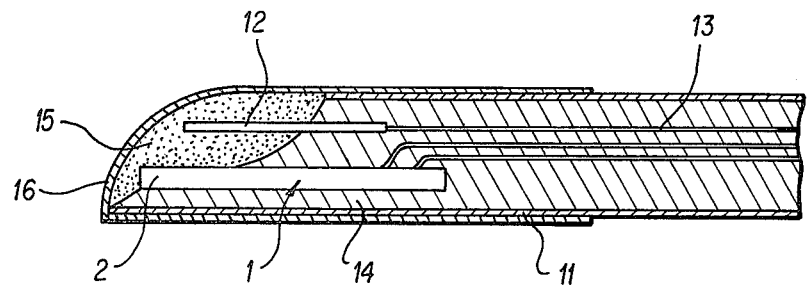
Figure 4:
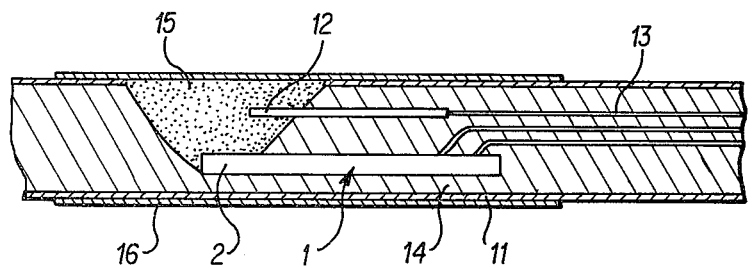

FIG. 3 is a sectional view of a gas sensor of the Severinghaus type of this invention using the aforementioned pH-ISFET. This sensor has a reference electrode 12 formed of Ag-AgCl wire and a pH-ISFET 1, which are separated from each other, housed in a flexible insulator tube 11 of polyethylene, polypropylene, polytetrafluoroethylene, silicone, nylon 11, polyvinylchloride, polyethylene-terephthalate, etc., for example, in the front end of a catheter which is insertable in the living body. The aforementioned reference electrode may be formed by depositing Ag-AgCl on the surface of the pH-ISFET, as shown in U.S. Pat. No. 4,409,980. Part of the aforementioned Ag-AgCl reference electrode and the gate part 2 of the pH-ISFET 1 are housed in the insulator tube 11, exposed at its front end opening. Respective lead wires 13 connected to the aforementioned reference electrode 12 and the pH-ISFET 1 are coated wth an insulator and led through the insulator tube and out from its rear end (not shown in this figure). The front end opening of the insulator tube 11 is projected somewhat from pH-ISFET 1 for its protection from damage and, moreover, obliquely cut, as shown in FIG. 3 (b), so as to ensure its easy insertion into the living body. Then an electrical insulation resin 14, for example, epoxy resin or silicone resin, etc., is filled in the space inside the part of the insulator tube wall housing the parts connecting the lead wires to the pH-ISFET 1 and the Ag-AgCl reference electrode 12, thereby closing at least the front end part of the insulator tube. The aforementioned insulation resin should desirably be filled in all inside space of the insulator tube. FIG. 4 presents another example of the gas sensor of this invention, in which the Ag-AgCl reference electrode 12 and the pH-ISFET 1 are housed in an insulator tube 11 under an opening provided in its side wall. The opened part of the insulator tube is closed by filling an electrical insulation resin 14 into the tube, leaving a space formed by the aforementioned opening, the gate part 2 of pH-ISFET and part of the reference electrode. Then a hydrophilic polymer layer 15 containing electrolytes which undergo change in pH as it absorbs gas is put around the gate part 2 of the pH-ISFET 1 and the reference electrode 12, enveloping both of them. This polymer layer should desirably have a thickness of 1-10 μm in dry state. As the thickness of the polymer layer grows more than 10 μm, the response speed becomes small, but if it is less than 1 μm, the signal becomes unstable. Accordingly, the polymer layer needs to be moderately thin and uniform.

It is essential that the polymer used here should have moderate water absorbency (higher than 60% by weight at the measuring temperature of 37° C.) and substantially contain no, or less than 2 mol% (of the total monomer units) of, organic acid radicals such as COOH radical nor base radicals. As the water absorbency declines, the response speed goes down and the organic acid radical or base radical, if contained in the polymer, causes reduction in sensitivity. Such polymers include polyvinyl alcohol (hereinafter referred to as PVA), cellulose, polyhydroxymethylmethacrylate, polyvinylpyrrolidone, agar-agar, starch, etc., and electrolyte polymers, etc. These polymers may be copolymers with other monomers or it may contain plasticizers, etc. Of these polymers, especially, PVA is excellent in stability.

With regard to the electrolyte contained in the polymer layer, if its concentration is low, sensitivity tends to be low, resulting in unstable signals. If its concentration is high, the response speed diminishes. Accordingly, the amount of the electrolyte contained needs to be in the range where such troubles do not occur. For example, in the case of carbon dioxide gas sensor, 0.01–1 mole/l of $NaHCO_3$ and 0.1–2 mole/l of NaCl should desirably be contained in the aqueous solution of polymer. The polymer layer containing such electrolytes may be formed by dissolving the polymer and electrolytes in a solvent to both of them, for example, water, and coating the solution on the objects, followed by drying. Or after applying a single solution of polymer or bridging, if required, the polymer layer obtained by making polymerization on the gate, the resultant polymer layer is swelled by dipping in an electrolyte solution, followed by drying.

With regard to a particular example of the aforementioned hydrophilic polymer, reference is made to that of U.S. Pat. No. 4,409,980.

The aforementioned polymer layer 15 is further coated with a gas permeable colored silicone rubber 16. In order to give always stable and correct measured values for a long period without being photosensitive, the aforementioned gas permeable membrane needs to have the following performances:

(1) The 90% response time of gas sensor shall be less than 120 sec; and
(2) The gas sensor shall have a photosensitivity less than 1 mV to a colorless light at 2,000 luxes. Where the 90% response time of a gas sensor is defined to be the period from the instant when the gas sensor is transferred from under 36 mmHg partial gas pressure at 37° C. to under 72 mmHg partial pressure until the output of the gas sensor reaches 90% of the equilibrium value. The output of the gas sensor is represented by the indication of the partial pressure of gas. The photosensitivity of a gas sensor is measured in the following manner: The gas sensor is placed in dark room in such a way that the gate surface of pH-ISFET is turned to a tungsten lamp at a distance therefrom where the illunination intensity is 2,000 luxes and the output from the gas sensor is taken out as the source potential. The drain current is fixed at 30 $\mu$A. At this time, the photosensitivity of the gas sensor is represented by the difference of the outputs of the gas sensor between when the gas sensor is illuminated by the tungsten lamp and when not.

The present inventors, in an effort to search for gas permeable membranes which satisfy the aforementioned two conditions, have made studies on their transmittance and gas permeability by adding dyes or pigments to fluorocarbon series polymers and copolymers of tetrafluoroethylene, trifluoroethylene, hexafluoropropylene, chlorotrifluoroethylene, etc., polyolefins such as polyethylene, polypropylene, polypentene-1, etc., and silicone, etc. The result revealed that as a pigment is added in increasing amounts, the transmittance decreases, but the gas permeability also declines and silicone rubber with intrinsically high gas permeability which shows adequate gas permeability, even after the pigment has been added, is advantageous.

It was found out that in order to meet, with the aforementioned silicone rubber, the required performances of a gas sensor abovementioned, i.e., less than 120 sec 90% response time and less than 1 mV/2,000 luxes photosensitivity, the photosensitivity of the pH-ISFET may be allayed by utilizing as the gas permeable membrane a silicone film which gives the nitrogen gas permeability at room temperature higher than $2.5 \times 10^{-7}$ $cm^3(STP)/cm^2 \cdot sec \cdot cmHg$ and the transmittance to a range of wave lengths of 400–1,200 m$\mu$ lower than 10%. The permeability of nitrogen gas abovementioned is the volume of the nitrogen gas which passes the membrane in 1 second, when the membrane area is 1 $cm^2$ and the partial pressure difference of nitrogen gas between both surfaces of the membrane is 1 cmHg, converted into its volume under the standard state (STP; 0° C. and 1 atmospheric pressure).

Further, it was found out that a modified silicone rubber membrane which should give the permeability to nitrogen gas higher than $2.5 \times 10^{-7}$ $cm^3$ $(STP)/cm^2 \cdot sec \cdot cmHg$ and the transmittance to 400–1,200 m$\mu$ lower than 10% is a silicone rubber membrane with a carbon black content which satisfies the conditions represented by the formulae (1), (2) and (3):

$$10 \leq d \leq 200 \qquad (1)$$

$$0.01 \leq dc/s \leq 0.50 \qquad (2)$$

$$c \leq 0.50 \qquad (3)$$

where s denotes the mean volume-surface particle diameter represented by angstrom unit; d the thickness of the silicone rubber membrane indicated by micrometer unit; and c the weight fraction of carbon black in the silicone rubber membrane.

The mean volume-surface particle diameter is defined by an equation (4):

$$s = \frac{\Sigma n_i s_i^3}{\Sigma n_i s_i^2} \qquad (4)$$

where $d_i$ stands for the diameter (Å) of each particle of carbon black observed under an electron microscope and $n_i$ the number of particles having the particle diameter of $d_i$. The diameter $s_i$ may be chosen at intervals of 50 angstroms.

The formula (1) shows the range of thicknesses of the silicone rubber membrane used in the gas sensor of this invention. Thus the thickness of the silicone rubber membrane needs to fall in the range of from 10 $\mu$m to 200 $\mu$m. If the thickness of the silicone rubber membrane is more than this range, the gas permeability becomes too low. Moreover, the OD of the whole of the sensor becomes too large and much pain will be afflicted on a patient, for example, when this sensor is left indwelling in the patient's blood vessel. If the thickness becomes less than the aforementioned range, pin holes will tend to be formed in the membrane and its mechanical strength decline. Thus its thicknesses outside this range are undesirable.

The formulae (2) and (3) define the range of carbon black contents in the silicone rubber membrane. Thus the carbon black content c needs to fall within the range from 0.01 s/d to 0.50 s/d and be not in excess of 0.5. If the carbon black content becomes less than that indicated by the formula (2), the transmittance to 400-1,200 nm will become higher than 10% and therefore, this is undesirable. If, on the other hand, the content of carbon black becomes more than the range of the formula (2), the gas permeability of silicone rubber diminishes or forming of the silicone rubber membrane becomes difficult, or its mechanical strength becomes inadequate, even if its forming is possible.

The aforementioned gas permeable membrane may be applied, as shown in FIG. 3 (b), by using the methods of dipping, spraying, etc. The gas permeable membrane needs to be a uniform thin film in order to have adequate response speed. For this purpose, as shown in FIG. 3 (a), it is possible to coat at least the part of the insulator tube surface, covering the pH-ISFET all-over, with a gas permeable tube closed at its front end with the aforementioned colored silicone rubber 17. Or in a sensor provided with an opening in the side wall of the insulator tube, a tubular silicone rubber may be coated on the insulator tube. This method is desirable, because it permits miniaturization of gas sensors, when they are oblong.

Figure 5:
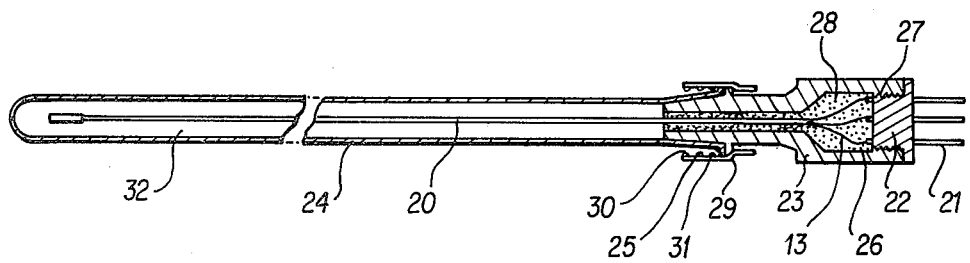
FIG. 5 is a sectional view of the gas sensor housed in a protector tube.

Since, its hydrophilic polymer layer being dry, the gas sensor manufactured in this way does not function, the hydrophilic polymer is swelled by letting it absorb moisture in water or steam, before putting this sensor to use. This sensor, even once dried, will become reusable by immersing it in water for a long period, but to ensure immediate use, the sensor should desirably be kept in water. FIG. 5 illustrates a gas sensor housed in a keeping container for preliminarily getting the hydrophilic polymer swell by absorbing moisture.

This gas sensor is composed of the catheter part 20 having the pH-ISFET and the Ag-AgCl reference electrode projected from the front end of the flexible tube, a connector 22 to which the lead wires 13 are connected, a plug 23 attached to the end part of the catheter part, a sleeve shape protective tube 24 and a rotary lock 25 for holding the plug and the protective tube in close liquid tight fit.

The catheter part 20 has pH-ISFET and Ag-AgCl reference electrode housed at the front end of an oblong flexible tube, as shown in FIG. 3. The lead wires 13 connected to the pH-ISFET and the reference electrode are extended along the inside wall of the tube and taken out through the opening at the other end.

To the connector 22, connector pins 21 are studded and to said pins, the aforementioned lead wires are connected with solder 26. The lead wire connecting part side of said connector is formed in a cylindrical shape and pins are securely set therein. On the outer circumference of said cylindrical part, a thread 27 is cut.

The plug 23 is in a cylindrical shape and in said plug, the catheter part 20 is inserted and one end of the plug is screwed on the aforementioned connector 22 through a thread 27. In the internal space of the cylindrical plug, an electrical insulation resin 28 is filled in, so that the end part of the tube forming the catheter part 20 and the lead wires are embedded and fixed therein. On the other end part of the plug, a flange 29 for staying a rotary lock is provided and on this flange, a cylindrical rotary lock 25 is fitted. The rotary lock 25 is so composed that its end part is engaged by the aforementioned flange 29. On the internal circumference of the cylindrical rotary lock, a spiral shape protrusion 30 is provided.

The protective tube 24 is in the shape of a sleeve made of a heat resistant resin and closed at one end and on the opening of said protective tube, there is provided a rotary lock retainer 31 which engages with the spiral protrusion 30 formed on the internal circumference of the aforementioned rotary lock 25. Inside this protective tube, a solution 32 having dissolved therein the conjugate ion to the gas to be detected is put in.

The conjugate ion put in the protective tube means a base ion being in conjugate relationship with the gas, when the gas is basic. For example, in the case of $CO_2$ sensor, the conjugate ions are $HCO_3^-$ and $CO_3^{2-}$ ions. Solutions containing these ions may be prepared by dissolving in solvents such salts as, for example, $NaHCO_3$, $KHCO_3$, $(NH_4)HCO_3$, $Na_2CO_3$, $K_2CO_3$, $(NH_4)CO_3$, etc. In the case of $SO_2$ sensor, the conjugate ions are $HSO_3^-$ and $SO_3^{2-}$; therefore, it is proper to use $NaHSO_3$, $KHSO_3$, $(NH_4)HSO_3$, $Na_2SO_3$, $K_2SO_3$, $(NH_4)SO_3$, etc. In the case of $NO_2$ sensor, 2 types, $NO_3^-$ and $NO_2^-$ are available as the conjugate ions; it is proper to use a solution containing at least one of them. Such a solution may be prepared by dissolving in some solvent at least one type of salt among $NaNO_3$, $KNO_3$, $NH_4NO_3$, $NaNO_2$, $KNO_2$ and $NH_4NO_2$, for example. Similarly, in the case of halogen gas sensors, the intended solution may be prepared by dissolving in some solvent at least one type of salt among $NaX$, $KX$, $NH_4X$, $NaXO$, $KXO$ and $NH_4XO$ ($X=Cl$, $Br$ and $I$). Solutions containing these conjugate ions are in use as the electrolytes contained in the hydrophilic polymer which composes the gas sensor. The composition of the solution put in the aforementioned protective tube may be same as that of the solution used as the aforementioned electrolytes, but it need not be same. For example, in the case of $CO_2$ sensor, as the electrolytes, an aqueous solution of $NaHCO_3$ and $NaCl$ is normally employed and as the solution to be put in the protective tube of the $CO_2$ sensor, the solution of the same composition as the abovementioned may be used, but using an aqueous solution of $NaHCO_3$ only or an aqueous solution of $KHCO_3$ only is all right.

The concentration of the conjugate ion contained in the solution of the aforementioned conjugate ion is normally in the range of from 0.01 to 5 mole/l. As solvents of such solutions, such polar solvents as water, ethylene glycol, diethylene glycol, propylene glycol, propylene carbonate, etc., or their mixed solvent are used.

After housing the catheter part in the protective tube in which an aqueous solution is put in such a way that the sensitive part of the sensor mounted on the front end of the catheter part is immersed in the aqueous solution, by engaging the rotary lock 25 mounted on the plug with the rotary lock retainer 31 provided on the opening end of the protective tube, the opening end of the protective tube is closely fitted on one side of the flange 29, and the one end part of the rotary lock on the other side of the flange, thereby liquid tightly coupling the plug 23 and the protective tube 24.

Figure 6:
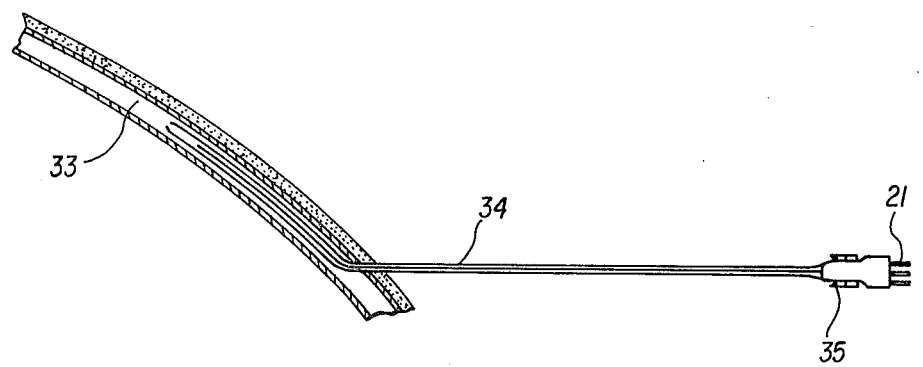
FIG. 6 is a sectional view showing the state of the gas sensor of this invention being inserted in a blood vessel.
Figure 7:
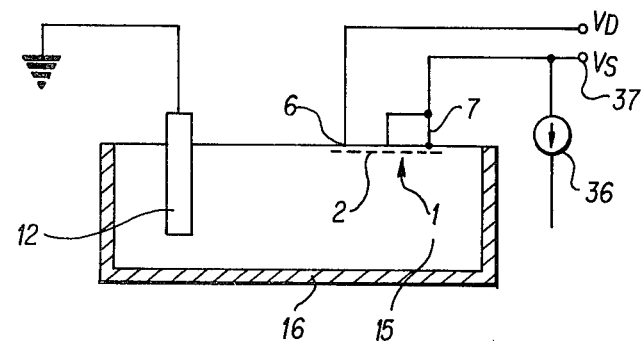
FIG. 7 is an electric circuit diagram of the gas sensor of this invention.

The gas sensor housed in the aforementioned protective tube, after being subjected to sterilization with high pressure steam, is preserved in wet state. The sensor taken out from the protective tube is inserted into the indwelling catheter 34 held inside a blood vessel 33, as shown in FIG. 6, for example, and by engaging the rotary lock 25 on the flange 35 provided on the indwelling catheter, the gas sensor may be liquid tightly inserted into the indwelling catheter. Then the measurement of the gas partial pressure in blood may be made by the circuit of FIG. 7, with the connector pins 21 of the aforementioned gas sensor linked to a monitor (not shown in the drawing).

This circuit is a source-follower circuit, with the reference electrode 12 grounded. On the drain 6, a constant voltage $V_D$ is impressed and across the drain 6 and the source 7, a constant current is passed by use of a constant current circuit 36. As the gas sensor is inserted into the liquid to be measured, e.g., blood vessel, the gas which has passed the gas permeable membrane 16 is absorbed by the electrolyte contained in the hydrophilic polymer layer 15, causing change in the hydrogen ion concentration in the electrolytes, thereby altering the surface potential of the gate part 2 of the pH-ISFET 1 exposed in the aforementioned polymer layer. With varying surface potentials, the source potential $V_s$ undergoes changes. Accordingly, by measuring the potential across the output terminal 37 and the reference electrode 12, the hydrogen ion concentration in the polymer layer, or the gas partial pressure in the solution, can be measured.

EXAMPLE 1

The pH-ISFET (length 5 mm and width 400 μm shown in FIG. 1 having $Si_3N_4$ as the sensitive film of the gate and an Ag-AgCl reference electrode formed by chlorinating a silver wire were embedded in the front end opening of a nylon catheter (0.6 mm diameter); over them, an aqueous solution of PVA containing $NaHCO_3$ and NaCl was applied; than, 8 types of colored silicone membranes which were all 100 μm thick, but which had different carbon black contents, were formed by using carbon black with mean volume-surface particle diameter 720 Å and silicone RTV, respectively coated on the aforementioned PVA film surface, thereby manufacturing the carbon dioxide gas sensors shown in FIG. 3 (b). Performances of the aforementioned 8 types of gas sensors are shown in Table 1.

TABLE 1

| Sensor No. | Carbon Black wt % | Transmittance % | $N_2$ Permeability $cm^3/cm^2 \cdot sec \cdot cmHg$ | 90% Response Time sec | Photo-response mV/2000 lux | $\frac{dc}{s}$ | Sensor performance |
|---|---|---|---|---|---|---|---|
| 1 | 0 | 98 | $3.0 \times 10^{-6}$ | 72 | 25 | 0 | x |
| 2 | 5 | 51 | $2.9 \times 10^{-6}$ | 76 | 12 | 0.007 | x |
| 3 | 10 | 9 | $1.5 \times 10^{-6}$ | 82 | 0.8 | 0.014 | o |
| 4 | 20 | 1.6 | $9.0 \times 10^{-7}$ | 96 | 0.3 | 0.028 | o |
| 5 | 40 | 0.2 | $4.2 \times 10^{-7}$ | 104 | 0.1 | 0.056 | o |
| 6 | 50 | 0.2 | $2.9 \times 10^{-7}$ | 110 | 0.1 | 0.069 | o |
| 7 | 60 | These membranes were mechanically very weak. | | | | | |
| 8 | 70 | | | | | | |

With increasing carbon black contents in the silicone rubber membranes, the transmittance (values taken at an 800 nm wave length) declines, resulting in reduced photosensitivity. When carbon black is more than approx. 10 wt.%, the transmittance at 800 nm declines to below 10% and therewith the photosensitivity of $PCO_2$ sensor goes down below 1 mV/2,000 luxes. On the other hand, the rate of permeation of nitrogen gas decreases with increasing carbon black contents, reaching $2.9 \times 10^{-7}$ $cm^3/cm^2 \cdot sec \cdot cmHg$ at 50 wt.%. The $PCO_2$ sensor's 90% response time is 110 sec. This indicates its practical usefulness. However, as the content of carbon black increases above 60 wt.%, the mechanical strengths of the silicon rubber membranes were very small so that the $PCO_2$ sensor failed to function in practical use.

EXAMPLE 2

Using as gas permeable membranes, 10 types of 102 μm thick blackened silicone rubber membranes differing in content of carbon black with mean volume-surface particle diameter 120 Å, carbon dioxide sensors shown in FIG. 3 (b) were manufactured by the same method as in Example 1. Performances of the aforementioned 10 types of carbon dioxide sensors are listed in Table 2:

TABLE 2

| Sensor No. | Carbon Black wt % | Transmittance % | $N_2$ Permeability $cm^3/cm^2 \cdot sec \cdot cmHg$ | 90% Response Time sec | Photo-response mV/2000 lux | $\frac{dc}{s}$ | Sensor performance |
|---|---|---|---|---|---|---|---|
| 9 | 0 | 98 | $3.0 \times 10^{-6}$ | 72 | 25 | 0 | x |
| 10 | 0.5 | 56 | $3.1 \times 10^{-6}$ | 71 | 14 | 0.004 | x |
| 11 | 0.7 | 24 | $3.0 \times 10^{-6}$ | 72 | 2 | 0.005 | x |
| 12 | 1.5 | 9.0 | $2.9 \times 10^{-6}$ | 72 | 0.9 | 0.013 | o |
| 13 | 2.0 | 3.6 | $2.9 \times 10^{-6}$ | 73 | 0.5 | 0.017 | o |
| 14 | 10 | 0.3 | $1.8 \times 10^{-6}$ | 79 | 0.1 | 0.085 | o |
| 15 | 20 | 0.2 | $1.0 \times 10^{-6}$ | 90 | 0.1 | 0.170 | o |
| 16 | 40 | 0.2 | $6.8 \times 10^{-7}$ | 100 | 0.1 | 0.340 | o |
| 17 | 50 | 0.1 | $5.0 \times 10^{-7}$ | 106 | 0.1 | 0.425 | o |
| 18 | 60 | This membrane was mechanically very weak. | | | | | |

In this instance, because the particle diameter of carbon black is smaller than that in Example 1, the transmittance at 400–1,200 nm is less than 10% for a carbon black content of 1.5 wt.%. If the carbon black content is more than 60 wt.%, the mechanical strengths of silicone rubber membranes are so small that they are of no practical use.

EXAMPLE 3

Performances of carbon dioxide sensors similar as those of Examples 1 and 2 which were manufactured using 180 μm thick silicone rubber membranes blackened with carbon black with its mean volume-surface diameter 120 Å are shown in Table 3.

TABLE 3

| Sensor No. | Carbon Black wt % | Transmittance % | $N_2$ Permeability $cm^3/cm^2 \cdot sec \cdot cmHg$ | 90% Response Time sec | Photo-response mV/2000 lux | $\dfrac{dc}{s}$ | Sensor performance |
|---|---|---|---|---|---|---|---|
| 19 | 0 | 97 | $1.7 \times 10^{-6}$ | 76 | 24 | 0 | x |
| 20 | 0.5 | 35 | $1.7 \times 10^{-6}$ | 76 | 11 | 0.008 | x |
| 21 | 0.7 | 8.1 | $1.6 \times 10^{-6}$ | 78 | 0.8 | 0.011 | o |
| 22 | 1.5 | 0.1 | $1.6 \times 10^{-6}$ | 79 | 0.1 | 0.023 | o |
| 23 | 2.0 | 0.1 | $1.5 \times 10^{-6}$ | 81 | 0.1 | 0.030 | o |
| 24 | 10 | 0.1 | $1.0 \times 10^{-6}$ | 92 | 0.1 | 0.150 | o |
| 25 | 20 | 0.1 | $5.4 \times 10^{-7}$ | 110 | 0.1 | 0.300 | o |
| 26 | 40 | 0.1 | $2.4 \times 10^{-7}$ | 135 | 0.1 | 0.600 | x |
| 27 | 50 | 0.1 | $2.1 \times 10^{-7}$ | 142 | 0.1 | 0.750 | x |

In this instance the thickness of the silicone rubber membrane is approx. 1.8 times as large as that in Example 2. For this reason, when the carbon black content is only 0.7 wt.%, the transmittance is already lower than 10%. On the other hand, due to the increased membrane thickness, the gas permeability diminishes; consequently, when the content of carbon black is at 40 and 50 wt.%, the gas permeability is lower than $2.5 \times 10^{-7}$ $cm^3/cm^2 \cdot sec \cdot cmHg$, even though the mechanical strength of the silicone rubber membrane is adequate, so that the 90% response time as a $PCO_2$ sensor is in excess of 120 sec.

EXAMPLE 4

An aqueous solution containing 0.1M of $NaHCO_3$ was put in a protective tube and in this tube, the catheter part of a carbon dioxide sensor of FIG. 3 (a) was inserted, and the tube was, then, hermetically plugged. After the carbon dioxide sensor hermetically plugged in this manner had been subjected to a high pressure steam sterilization at 120° C. for 1 hr, it was left cooling until the temperature went down to the room temperature. Then the catheter part was taken out of the protective tube. The front end of the catheter housing the pH-ISFET and the reference electrode were immersed in water held at 37° C. and being in equilibrium state with 5% (36 mmHg) $CO_2$ and the vicissitude with time of the zero source potential was measured with the circuit shown in FIG. 7. The drifts in the source potential at 10 minutes, 1 hour and 24 hours after its immersion were, respectively, +5 mV, +5 mV and +6 mV. Thus the drifts of the carbon dioxide sensor had settled within 10 min after starting the measurement and thereafter, the drift was on the order of +1 mV in 24 hr.

Comparative example

Simple distilled water was put in the protective tube shown in FIG. 5 and in this tube, the catheter part of the carbon dioxide gas sensor was inserted. The tube was, then, hermetically plugged and thereafter, was subjected to sterilization similarly as in Example 1. After the sterilization was made, the protective tube was left cooling down to the room temperature and when the changes in the source potential under the similar conditions as in Example 1 were measured, the drift values in the source potential 10 min, 1 hr and 24 hr after starting the measurement were, respectively, +45 mV, +92 mV and +143 mV.

What is claimed is:

1. A gas sensor composed of a hydrogen ion sensitive FET transducer of an oblong gate-insulated field effect transistor structure having the gate part at its front end and the electrode part at the other end, an Ag-AgCl reference electrode placed adjacent the gate part of the aforementioned transducer, an insulator tube housing the FET transducer and the reference electrode to each of which one end of a lead wire is connected, the FET transducer and the reference electrode being located at an opening part provided in the insulator tube, and the lead wires extended along the tube, with a connector joined to the other end of said lead wire, an electrical insulation resin which is filled at least in the space of the part inside the tube wall housing the lead wire connecting parts, thereby closing the tube, a hydrophilic polymer layer put around the gate part of the FET transducer and the reference electrode, enveloping both of them, said layer containing electrolytes which undergo changes in hydrogen ion concentration, as it absorbs gas, and a gas permeable membrane formed of a colored silicone rubber which gives transmittance less than 10% and the division (P/d) of the gas permeability of nitrogen (P) by the membrane thickness (d) is larger than $2.5 \times 10^{-7}[cm^3(STP)/\, cm^2 \cdot sec \cdot cmHg]$, said membrane coating the whole of the aforementioned hydrophilic polymer layer and the whole of the surface of at least the part of the insulator tube in which the FET transducer is housed.

2. A gas sensor according to claim 1, wherein the gas permeable membrane is a black silicone rubber having a film thickness of 10 μm–200 μm and a carbon black content which satisfies the following formulae:

$$0.01 \leq dc/s \leq 0.50$$

$$c \leq 0.50$$

where
  d: Film thickness (μm) of silicone rubber
  s: Mean volume-surface particle diameter of carbon black contained in silicone rubber (Å)
  c: Weight fraction of carbon black in silicone rubber.

3. A gas sensor according to claim 1, wherein the gas permeable membrane is a tube shape colored silicone rubber which is liquid tightly coated on the insulator tube.

4. A gas sensor according to claim 1, wherein the insulator tube is a flexible capillary tube which is so composed as to be inserted in living bodies.

5. A gas sensor according to claim 1, wherein the insulator tube housing the gas sensitive part
  is liquid tightly inserted in a protective tube containing a solution in which at least one type of conjugate ion to the gas to be detected is dissolved.

* * * * *